(12) United States Patent
Tokarski et al.

(10) Patent No.: US 12,674,210 B2
(45) Date of Patent: Jul. 7, 2026

(54) AMPLIFICATION PRIMER KIT, A METHOD FOR DETECTING A SEXUALLY TRANSMITTED BACTERIAL INFECTION, AND A KIT FOR DETECTING THE INFECTION

(71) Applicant: GENOMTEC S.A., Wroclaw (PL)

(72) Inventors: Miron Tokarski, Brzeg (PL); Izabela Pielka, Konopiska (PL); Malgorzata Malodobra-Mazur, Wroclaw (PL)

(73) Assignee: Genomtec S.A., Wroclaw (PL)

( * ) Notice: Subject to any disclaimer, the term of this patent is extended or adjusted under 35 U.S.C. 154(b) by 433 days.

(21) Appl. No.: 18/549,736

(22) PCT Filed: Mar. 12, 2022

(86) PCT No.: PCT/PL2022/050014
§ 371 (c)(1),
(2) Date: Sep. 8, 2023

(87) PCT Pub. No.: WO2022/191726
PCT Pub. Date: Sep. 15, 2022

(65) Prior Publication Data
US 2025/0277276 A1 Sep. 4, 2025

(30) Foreign Application Priority Data
Mar. 12, 2021 (PL) ........................................ 437280

(51) Int. Cl.
*C12Q 1/689* (2018.01)
*C12Q 1/6844* (2018.01)

(52) U.S. Cl.
CPC ........... *C12Q 1/689* (2013.01); *C12Q 1/6844* (2013.01); *C12Q 2600/156* (2013.01)

(58) Field of Classification Search
CPC .. C12Q 1/689; C12Q 1/6844; C12Q 2600/16; C12Q 2527/101; C12Q 2537/143; C12Q 2563/107
See application file for complete search history.

(56) References Cited

U.S. PATENT DOCUMENTS

2021/0024980 A1* 1/2021 Dedent .................. C12Q 1/689

FOREIGN PATENT DOCUMENTS

EP          0872561 A2 * 10/1998 .......... C12N 9/1007
WO      2017103269 A1    6/2017
WO    WO-2018089945 A1 *  5/2018 ............. C12Q 1/689

OTHER PUBLICATIONS

Chen X, et al. Frontiers in Molecular Biosciences. 8. 2021. 702134 (Year: 2021).*
Shimuta K, et al. Antimicrobial Agents and Chemotherapy. 64(1). 2019. 10-1128 (Year: 2019).*
Liu et al. Loop-mediated isothermal amplification of Neisseria gonorrhoeae porA pseudogene: a rapid and reliable method to detect gonorrhea, AMB Express. 2017, 7(1), 48, 1-7.
(Continued)

*Primary Examiner* — Samuel C Woolwine
*Assistant Examiner* — Kara N Kovach
(74) *Attorney, Agent, or Firm* — Arrigo, Lee, Guttman & Mouta-Bellum LLP

(57) ABSTRACT

The invention relates to a set of amplification primers, a method for detecting a sexually transmitted bacterial infection, and a kit for detecting the infection.

12 Claims, 2 Drawing Sheets
Specification includes a Sequence Listing.

(56) References Cited

OTHER PUBLICATIONS

Edwards et al. Loop-mediated isothermal amplification test for detection of Neisseria gonorrhoeae in urine samples and tolerance of the assay to the presence of urea, J Clin Microbiol. 2014, 52(6), 2163-2165.

* cited by examiner

SEQUENCE LISTING

```
<160> NUMBER OF SEQ ID NOS: 9

<210> SEQ ID NO 1
<211> LENGTH: 18
<212> TYPE: DNA
<213> ORGANISM: artificial
<220> FEATURE:
<223> OTHER INFORMATION: primer

<400> SEQUENCE: 1
tatgagccgg aaccgagt                                                    18

<210> SEQ ID NO 2
<211> LENGTH: 19
<212> TYPE: DNA
<213> ORGANISM: artificial
<220> FEATURE:
<223> OTHER INFORMATION: primer

<400> SEQUENCE: 2
tcgggaaagc cttggattc                                                   19

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
atctttgggg cttgcgggtg                                                  20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
taaagcgtgg gatgaacagg                                                  20

<210> SEQ ID NO 5
<211> LENGTH: 20
```

<212> TYPE: DNA
<213> ORGANISM: artificial
<220> FEATURE:
<223> OTHER INFORMATION: primer

<400> SEQUENCE: 5
aagcacgggg caaacgacta                                                  20

<210> SEQ ID NO 6
<211> LENGTH: 19
<212> TYPE: DNA
<213> ORGANISM: artificial
<220> FEATURE:
<223> OTHER INFORMATION: primer

<400> SEQUENCE: 6
caacttcgcg taccgtcat                                                   19

<210> SEQ ID NO 7
<211> LENGTH: 22
<212> TYPE: DNA
<213> ORGANISM: artificial
<220> FEATURE:
<223> OTHER INFORMATION: primer

<400> SEQUENCE: 7
cctgaagctt ggacggtaaa ac                                               22

<210> SEQ ID NO 8
<211> LENGTH: 24
<212> TYPE: DNA
<213> ORGANISM: artificial
<220> FEATURE:
<223> OTHER INFORMATION: primer

<400> SEQUENCE: 8
gccggcaaag aaacactata tcgg                                             24

<210> SEQ ID NO 9
<211> LENGTH: 1026
<212> TYPE: DNA
<213> ORGANISM: Neisseria gonorhoeae

<400> SEQUENCE: 9
atgcaaaact catcacctac cacttataat cctatgaaaa tcattagttt gtttagcggt    60
tgcggcggtt tggatttggg tttcgaaaaa gcgggatttg aaatccccgc cgccaacgaa   120
tacgataaaa ccatttgggc aaccttcaag gcaaaccatc caaagaccca tttgatagaa   180
ggcgatatac gcaagattaa agaagaagat ttccctgaag aaatcgacgg gattatcggc   240
ggcccaccct gccagtcttg gtctgaagcg ggagctttgc gcggcatcga cgatgcgcgc   300
ggacagttgt ttttcgacta catccgtatt ttgaaaagca aacagccaaa attcttttta   360
gcggaaaacg tcagcggaat gctggcaaac cgccacaacg gagccgtaca aaacctgctg   420
aaaatgtttg acggatgcgg atacgacgta accttgacta tggccaacgc caaagactac   480
ggtgtagcac aggaacgcaa aagggtcttc tacatcggtt tccgtaaaga cttggaaata   540
aaattttctt ttccaaaagg ttcgacggtc gaagacaaag acaagattac attgaaagac   600
gttatttggg atttgcagga cacagccgta ccttccgccc cgcaaaacaa gaccaacccc   660
gacgcagtca acaacaacga atattttacc ggcagttttt cccctatttt tatgagccgg   720
aaccgagtta aagcgtggga tgaacagggt tttaccgtcc aagcttcagg caggcagtgc   780

-continued

```
caactgcacc cgcaagcccc aaagatggaa aagcacgggg caaacgacta ccgttttgct     840
gccggcaaag aaacactata tcggaggatg acggtacgcg aagttgcaag aatccaaggc     900
tttcccgaca acttcaaatt catctatcaa aatgtcaacg acgcatacaa aatgattggc     960
aacgccgtcc ccgtcaacct tgcctacgaa attgcagcgg caattaaaaa aaccctagaa    1020
aggtga                                                              1026
```

AMPLIFICATION PRIMER KIT, A METHOD FOR DETECTING A SEXUALLY TRANSMITTED BACTERIAL INFECTION, AND A KIT FOR DETECTING THE INFECTION

SEQUENCE LISTING

The instant application contains a Sequence Listing which has been submitted electronically in ASCII format and is hereby incorporated by reference in its entirety. Said ASCII copy, created on Jan. 5, 2024, is named 18549736_ST25. txt and is 3,216 bytes in size.

FIELD OF THE INVENTION

The invention relates to a set of primers for detecting *Neisseria gonorrhoeae* (NG) bacteria, a method for detecting *Neisseria gonorrhoeae* using the set of primers, and the use of the set of primers for detecting *Neisseria gonorrhoeae*. The invention is applicable in medical diagnostics.

BACKGROUND OF THE INVENTION

*Neisseria gonorrhoeae* is a gram-negative bacterium. It is classified as a sexually transmitted disease (STD) pathogen. Also, newborns may become infected during childbirth. The infections mainly affect the urethra, but also the cervical canal, rectum, pharynx and conjunctiva. In Europe, infections with the *Neisseria gonorrhoeae* bacterium are the second most common sexually transmitted infections, after chlamydial infections.

Laboratory diagnosis of *Neisseria gonorrhoeae* bacteria is based primarily on detecting bacteria in the secretions from the genitourinary tract or swabs collected from body parts that are possible to be infected. Possible methods of detecting *Neisseria gonorrhoeae* bacteria are culture, microscopic methods after staining (Gram or methylene blue) or genetic tests, including the most commonly used Real-Time PCR. Post-staining microscopic tests are characterized by a relatively low sensitivity, especially in the case of asymptomatic infection (<55%), and in the case of rectal infections, even <40%. On the other hand, the culture tests, despite their high sensitivity and specificity, are labour-intensive and time-consuming tests. In addition, the cultures of *Neisseria gonorrhoeae* require specific, selective media.

The methods characterized by the greatest specificity and sensitivity are those involving the detection of *Neisseria gonorrhoae* nucleic acid in biological material (the so-called NAAT methods—Nucleic Acid Amplification Tests), i.e., in the urine or urethral swab in men and vaginal or urethral swab in women, moreover in throat or mucosa swabs. The most commonly used tests in NAAT technology are Real-Time PCR-based assays. Many different tests using the Real-Time PCR technique are available on the market, but despite the fierce competition, these methods are still relatively expensive. Moreover, they require highly specialized personnel, expensive devices, and the isolation of genetic material from the patient's sample is necessary. Moreover, since cyclic heating and cooling of the reagents is necessary, this method is long, and the devices used consume relatively large amounts of energy to carry out this process.

Isothermal methods, including the LAMP (Loop-mediated isothermal amplification) method, are methods that allow to accelerate the diagnostic process and reduce the cost of energy needed to perform the analysis. Moreover, according to the literature data, these methods are characterized by higher sensitivity and specificity than the aforementioned Real-Time PCR technique, they are also much faster. Their isothermal course does not require specialized equipment.

Due to the low equipment requirements, isothermal methods are an ideal diagnostic solution for primary care units (POCT—point-of-care testing), where the test can be performed in the practice of a general practitioner or specialist doctor (gynaecologist, urologist) at the first contact of a patient with the doctor. This solution allows for a short turn-around-time (in no more than 15 minutes), which allows for selection of a targeted therapy during the very first visit. This is especially important in the case of the so-called progressive *Neisseria gonorrhoeae* infection, which can lead to bacteraemia, where prompt diagnosis and early treatment are extremely important. On the other hand, the use of freeze-dried reagents allows the tests to be stored at room temperature, without the need to freeze the diagnostic tests.

The use of primers in the LAMP method for the diagnosis of *Neisseria gonorrhoeae* is known from the patent applications published so far: CN101831488A; CA3008949A1; WO2016023397A1; ES2773313T3; US20190284618A1; U.S. Pat. No. 10,047,404B2. The LAMP method is disclosed, for example, in patent specifications WO0028082, WO0224902. The above-mentioned patent applications in most cases do not describe the sensitivity and detection limit of *Neisseria gonorrhoeae*. The detection method in some of the above-mentioned patent applications does not allow for quantitative measurement, and the detection is of the endpoint type, using agarose gel electrophoresis or other markers based on the colour change of the reaction mixture upon a positive result of the amplification reaction. Some patent applications are implemented in the Real-Time technology, which enables quantitative measurement, but the detection method is based on molecular probes labelled with fluorescent dyes, which significantly increases the costs of the analysis. Moreover, in the described patent applications, the analysis time and time-to-positive result is about 60 minutes. Besides, most of the kits developed and described above are not applicable in POCT diagnostics, and their main application is in laboratories.

Therefore, there is still a need to provide a diagnostic method using appropriately refined sets of primers used for the diagnosis of *Neisseria gonorrhoeae* with the LAMP method, intended for use in point-of-care testing, which allows the detection of bacteria with a very low detection limit (≥10 copies/reaction) in a short time (≤20 min). Unexpectedly, the above problem was solved by the present invention.

BRIEF SUMMARY OF THE INVENTION

The first subject of the invention is a set of primers for amplifying the nucleotide sequence of the *Neisseria gonorrhoeae* DNA cytosine methyltransferase (dcm) gene, characterized in that it contains a set of internal primers with the following nucleotide sequences a) and b), as well as a set of external primers containing the following nucleotide sequences c) and d) specific for a selected fragment of the *Neisseria gonorrhoeae* DNA cytosine methyltransferase (dcm) gene:

a) 5' ATCTTTGGGGCTTGCGGGTG 3' (nucleic sequence SEQ ID NO: 3 or its reverse and complementary sequence, linked from the 3' end, preferably by a TTTT bridge, to the sequence 5' TAAAGCGTGG- GATGAACAGG 3'-(nucleic sequence SEQ ID NO: 4 or its reverse and complementary sequence;

b) 5' AAGCACGGGGCAAACGACTA 3'-(nucleic sequence SEQ ID NO: 5 or its reverse and complementary sequence, linked from the 3' end, preferably by a TTTT bridge, to the sequence 5' CAACTTCGCGTACCGTCAT 3'-(nucleic sequence SEQ ID NO: 6 or its reverse and complementary sequence;

c) 5' TATGAGCCGGAACCGAGT 3' nucleic sequence SEQ ID NO: 1 or its reverse and complementary sequence, and d) 5' TCGGGAAAGCCTTGGATTC 3' nucleic sequence SEQ ID NO: 2 or its reverse and complementary sequence.

In a preferred embodiment of the invention the primer set comprises a set of loop primer sequences comprising nucleic sequences contained in or complementary to the *Neisseria gonorrhoeae* don gene SEQ ID NO: 7-5' CCT-GAAGCTTGGACGGTAAAAC 3' and SEQ ID NO: 8: 5' GCCGGCAAAGAAACACTATATCGG 3' or sequences reverse and complementary thereof.

The second subject of the invention is a method for detecting *Neisseria gonorrhoeae* bacteria, characterized in that a selected region of the nucleotide sequence of the *Neisseria gonorrhoeae* genome (DNA cytosine methyltransferase gene fragment) is amplified using a primer set as defined in the first subject of the invention, the amplification method being the LAMP method.

In a preferred embodiment, the amplification is carried out with a temperature profile of: 69° C., 40 min.

In a further preferred embodiment of the invention, the end-point reaction is carried out with an additional stage of temperature of 80° C., 5 min.

The third subject of the invention is a method for detecting an infection caused by the *Neisseria gonorrhoeae* bacterium, characterized in that it comprises the detection method defined in the second subject of the invention.

The fourth subject of the invention is a kit for the detection of an infection caused by *Neisseria gonorrhoeae*, characterized in that it comprises a set of primers as defined in the first subject of the invention.

In a preferred embodiment of the invention, the infection detection kit comprises 5.0 μl of WARMSTART LAMP Master Mix.

In a further preferred embodiment of the invention, individual amplification primers as defined in the first subject of the invention, the primers having the following concentrations: 0.12 μM F3, 0.12 μM B3, 0.96 μM FIP, 0.96 μM BIP, 0.24 μM LoopF, 0.24 μM LoopB; D-(+)-Trehalose dihydrate-6%; mannitol-1.25%; fluorescent marker interacting with double-stranded DNA-EVAGREEN® ≤1× (BIOTIUM) or FLUORESCENT DYE (NEW ENGLAND BIOLABS®) in the amount of ≤0.5 μl or GREENFLUO-RESCENT Dye (LUCIGEN) in the amount of ≤1 μl or SYTO-13≤16 μM (THERMOFISHER SCIENTIFIC) or SYTO-82≤16 μM (THERMOFISHER SCIENTIFIC) or another fluorescent dye interacting with double-stranded DNA at a concentration that does not inhibit the amplification reaction.

The advantage of the primer sets of the invention for the detection of *Neisseria gonorrhoeae*, as well as the method for detecting *Neisseria gonorrhoeae* infection and the method of detecting the amplification products is the possibility of using them in medical diagnostics at the point of care (POCT) in the target application with a portable genetic analyzer. Freeze-drying of the reaction mixtures of the invention allows the diagnostic kits to be stored at room temperature without reducing the diagnostic parameters of the tests. In turn, the use of a fluorescent dye to detect the amplification product increases the sensitivity of the method, allows to lower the detection limit (down to 10 genome copies/reaction), as well as it enables the quantitative measurement of bacteria in the test sample.

BRIEF DESCRIPTION OF THE DRAWINGS

Exemplary embodiments of the invention are presented in the drawing, in which:

FIG. 3: lane 1: mass marker (Quick-Load® Purple 100 bp DNA Ladder, NEW ENGLAND BIOLABS®); lanes 2 and 3: methicillin-sensitive *Staphylococcus aureus* (MSSA); lanes 4 and 5: methicillin-resistant *Staphylococcus aureus* (MRSA); lanes 6 and 7: *Chlamydia trachomatis* serovar D; lanes 8 and 9: *Chlamydia trachomatis* serovar G; lanes 10 and 11: *Chlamydia trachomatis* serovar J; lanes 12 and 13: *Chlamydia trachomatis* serovar H; lanes 14 and 15: *Chlamydia trachomatis* serovar E; lanes 16 and 17: *Neisseria meningitidis*; lanes 18 and 19: *Klebsiella pneumoniae;* lanes 20 and 21: *Bordetella pertussis*; lanes 22 and 23: *Enterococcus faecalis*; lanes 24 and 25: *Staphylococcus epidermidis; lanes* 26 and 27: *Pseudomonas aeruginosa*; lanes 28 and 29: *Streptococcus agalactiae*; lane 30: mass marker (Quick-Load® Purple 100 bp DNA Ladder, NEW ENGLAND BIOLABS®); lanes 31 and 32: *Listeria monocytogenes*; lanes 33 and 34: *Mycoplasma hominis*; lanes 35 and 36: *Haemophilus ducreyi*; lanes 37 and 38: human DNA; lanes 39 and 40: *Escherichia coli*; lanes 41 and 42: *Lactobacillus* gasseri; lanes 43 and 44: *Lactobacillus jensenii*; lanes 45,46: *Bacteroides fragilis;* 47, 48: *Toxoplasma gondii;* 49, 50: *Chlamydia trachomatis* serovar I; 51,52: *Chlamydia trachomatis* serovar II; 53,54: *Chlamydia trachomatis* serovar III; 55, 56: *Trichomonas vaginalis;* 57,58: *Gardnerella vaginalis * and FIG. 4: lane 1: mass marker (Quick-Load® Purple 100 bp DNA Ladder, NEW ENGLAND BIOLABS®); lanes 2 and 3: *Ureaplasma urealyticum*; lanes 4 and 5: *Campylobacter jejuni*; lanes 6 and 7: *Candida albicans*; lanes 8 and 9: HHV2; lanes 10 and 11: HSV2; lanes 12 and 13: HSV5; lanes 14 and 15: HPV 16; lane 16: mass marker (Quick-Load® Purple 100 bp DNA Ladder, NEW ENGLAND BIOLABS®); lanes 17 and 18:

Figure 1:
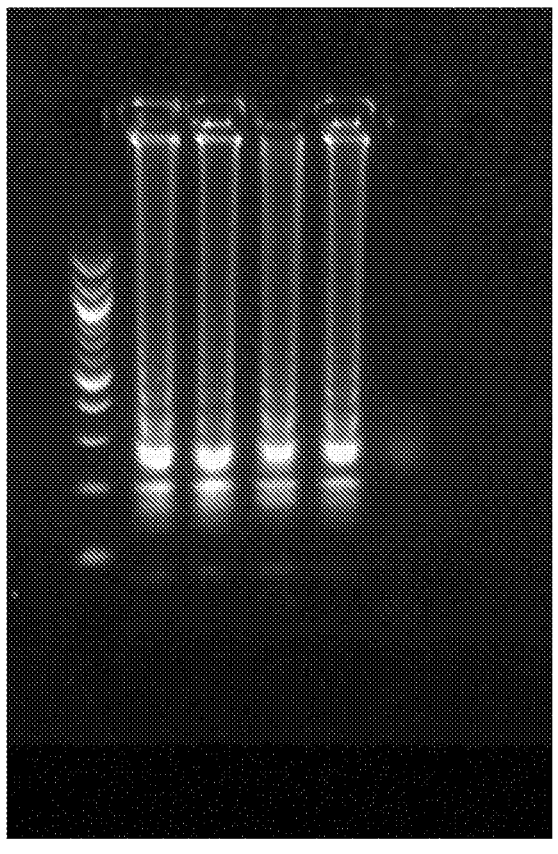
FIG. 1 shows the sensitivity characteristics of the method, where a specific signal was obtained with the template: *Neisseria gonorrhoeae* Quantitative DNA (ATCC® 700825DQ™) over the range of 100-10 copies/μl, but there was no product in NTC, where lane 1: mass marker (Quick-Load® Purple 100 bp DNA Ladder, NEW ENGLAND BIOLABS®); lane 2:100 copies of NG; lane 3:50 copies of NG; lane 4:20 copies of NG; line 5:10 copies of NG; lane 6: NTC.

HPV 18; lanes 19 and 20: HBV; lanes 21 and 22: *Mycoplasma genitalium*; lanes 23 and 24: *Neisseria gonorrhoeae*; lanes 25 and 26: NTC.

DETAILED DESCRIPTION OF THE INVENTION

Example 1 Primer Sequences

The sequences of specific oligonucleotides used for the detection of the *Neisseria gonorrhoeae* genetic material using LAMP technology are presented and characterized below.

1. The NG dcmF3 oligonucleotide sequence: 5' TATGAGCCGGAACCGAGT 3' (SEQ ID NO: 1) is identical to the *Neisseria gonorrhoeae* dcm gene (5'-3' strand) which is 3' end adjacent to the F2 primer.
2. The NG dcmB3 oligonucleotide sequence: 5' TCGGGAAAGCCTTGGATTC 3' (SEQ ID NO: 2) is a complementary fragment of the *Neisseria gonorrhoeae* dcm gene (5'-3' strand) 161 nucleotides away from the 3' end of the oligonucleotide 1.
3. The NG dcmF2 oligonucleotide sequence: 5' TAAAGCGTGGGATGAACAGG 3' (SEQ ID NO: 4) is a sequence identical to the *Neisseria gonorrhoeae* dcm gene (5'-3' strand) immediately adjacent to the 3' end of the oligonucleotide 1.
4. The NG dcmB2 oligonucleotide sequence: 5' CAACTTCGCGTACCGTCAT 3' (SEQ ID NO: 6) is a complementary fragment of the *Neisseria gonorrhoeae* dcm gene (5'-3' strand) 139 nucleotides away from the 3' end of the oligonucleotide 1.
5. The NG dcmF1c oligonucleotide sequence: 5' ATCTTTGGGGCTTGCGGGTG 3' (SEQ ID NO:3) is a complementary fragment of the *Neisseria gonorrhoeae* dcm gene (5'-3' strand) 58 nucleotides away from the 3' end of the oligonucleotide 1.
6. The NG dcmB1c oligonucleotide sequence: 5' AAGCACGGGGCAAACGACTA 3' (SEQ ID NO: 5) is a sequence identical to the *Neisseria gonorrhoeae* dcm gene (5'-3' strand) 82 nucleotides away from the 3' end of the oligonucleotide 1.
7. The NG dcmLoopF oligonucleotide sequence: 5' CCTGAAGCTTGGACGGTAAAAC 3' (SEQ ID NO: 7).
8. The NG dcmLoopB oligonucleotide sequence: 5' GCCGGCAAAGAAACACTATATCGG 3' (SEQ ID NO: 8).

The sequences of the F1c and F2 oligonucleotides have preferably been linked by a TTTT bridge and used as FIP. The sequences of the B1c and B2 oligonucleotides have preferably been linked by a TTTT bridge and used as BIP.

Example 2

Method of amplifying the *Neisseria gonorrhoeae* dcm gene using the oligonucleotides characterized in Example 1 with LAMP technology and the following composition of the reaction mixture:

5.0 μl WARMSTART LAMP 2× Master Mix
0.12 μM F3
0.12 μM B3
0.96 μM FIP
0.96 μM BIP
0.24 μM LoopF
0.24 μM LoopB
D-(+)-Trehalose dihydrate-6%
Mannitol-1.25%

Fluorescent marker interacting with double-stranded DNA-EVAGREEN® ≤1× or FLUORESCENT DYE 50× (NEW ENGLAND BIOLABS®) in the amount of 0.5 μl or GREENFLUORESCENT Dye (LUCIGEN) in the amount of ≤1 μl or SYTO-13≤16 μM or SYTO-82≤16 μM or another fluorescent dye that interacts with double-stranded DNA at a concentration that does not inhibit the amplification reaction.

DNA template ≥10 copies/reaction

Total reaction volume adjusted to 10 μl with DNase and RNase free water.

Example 3

Method of amplifying the *Neisseria gonorrhoeae* dcm gene using the oligonucleotides characterized in Example 1 and Example 2 with LAMP technology and the composition of the reaction mixture characterized in Example 3 with the following temperature profile:
1) 69° C., 40 min
2) preferably for end-point reactions 80° C., 5 min.

Example 4

Method of amplification and detection of the *Neisseria gonorrhoeae* dcm gene using the oligonucleotides characterized in Example 1 and Example 2 with LAMP technology and the composition of the reaction mixture characterized in Example 3 with the temperature profile characterized in Example 4 and the detection method described below.

A fluorescent dye is used, capable of interacting with double-stranded DNA, added to the reaction mixture in an amount of 0.5 μl EVAGREEN® 20×; 0.5 μL or a concentration of ≤1×; ≤16 μM respectively for GREENFLUORESCENT Dye (LUCIGEN); SYTO-13 and SYTO-82 before starting the reaction, real-time and/or end-point measurement. Excitation wavelength in the range similar to the FAM dye-490-500 nm (optimally 494 nm) for EVAGREEN®; FLUORESCENT DYE 50× (NEW ENGLAND BIOLABS®), GREENFLUORESCENT Dye (LUCIGEN); SYTO-13 dyes and 535 nm (optimally 541 nm) for SYTO-82 dye; emission wavelength in the range 509-530 nm (optimally 518 nm) for EVAGREEN®; GREENFLUORESCENT Dye (LUCIGEN); SYTO-13 dyes and 556 nm (optimally 560 nm) for SYTO-82 dye, the method of detection, change recording time starting from 11 minutes from the start of the reaction for *Neisseria gonorrhoeae* and the negative control.

Example 5

The method of preparation and freeze-drying of reagents for detecting the amplification and detection of the *Neisseria gonorrhoeae* dcm gene using the oligonucleotides characterized in Example 1 and Example 2 with LAMP technology and the composition of the reaction mixture characterized in Example 3 with the temperature profile characterized in Example 4 and the detection method described in Example 5.

Example 6. Description of the Freeze-Drying Process

The reaction components were mixed according to the composition described in Example 3, except the template DNA, to a total volume of 10 μl. The mixture was transferred to 0.2 ml tubes and subjected to the freeze-drying process according to the parameters below.

The mixture placed in the test tubes was pre-cooled to −80° C. for 2 hours. Then the freeze-drying process was carried out at the temperature of −80° C. for 3 hours under the pressure of $5^{-2}$ mBar.

Example 7. Sensitivity of the Method

Figure 2:
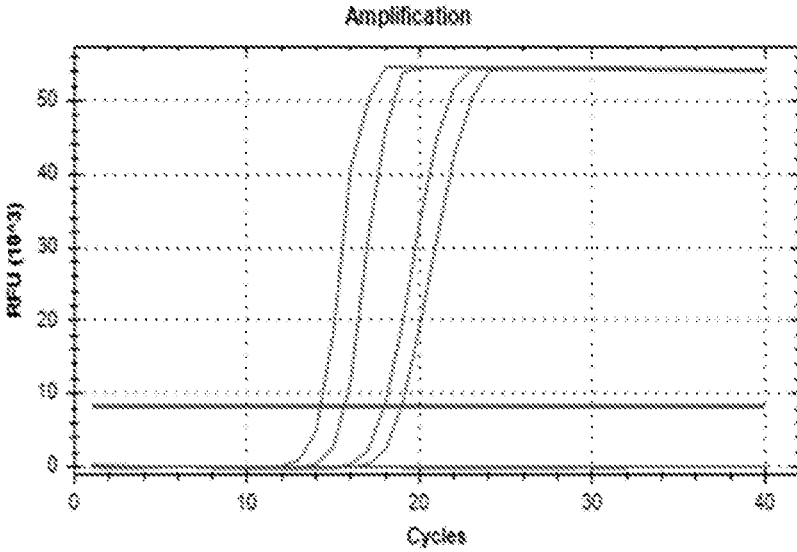
FIG. 2 shows the sensitivity of the method of the invention measured by assaying a serial dilution of the *Neisseria gonorrhoeae* Quantitative DNA (ATCC® 700825DQ™) standard over a range of 100-10 copies/reaction of the DNA standard, where the product amplification was measured in real time. The results of the real-time *Neisseria gonorrhoeae* detection are shown in Table 1, giving the minimum time required to detect the fluorescence signal.
Figure 3:
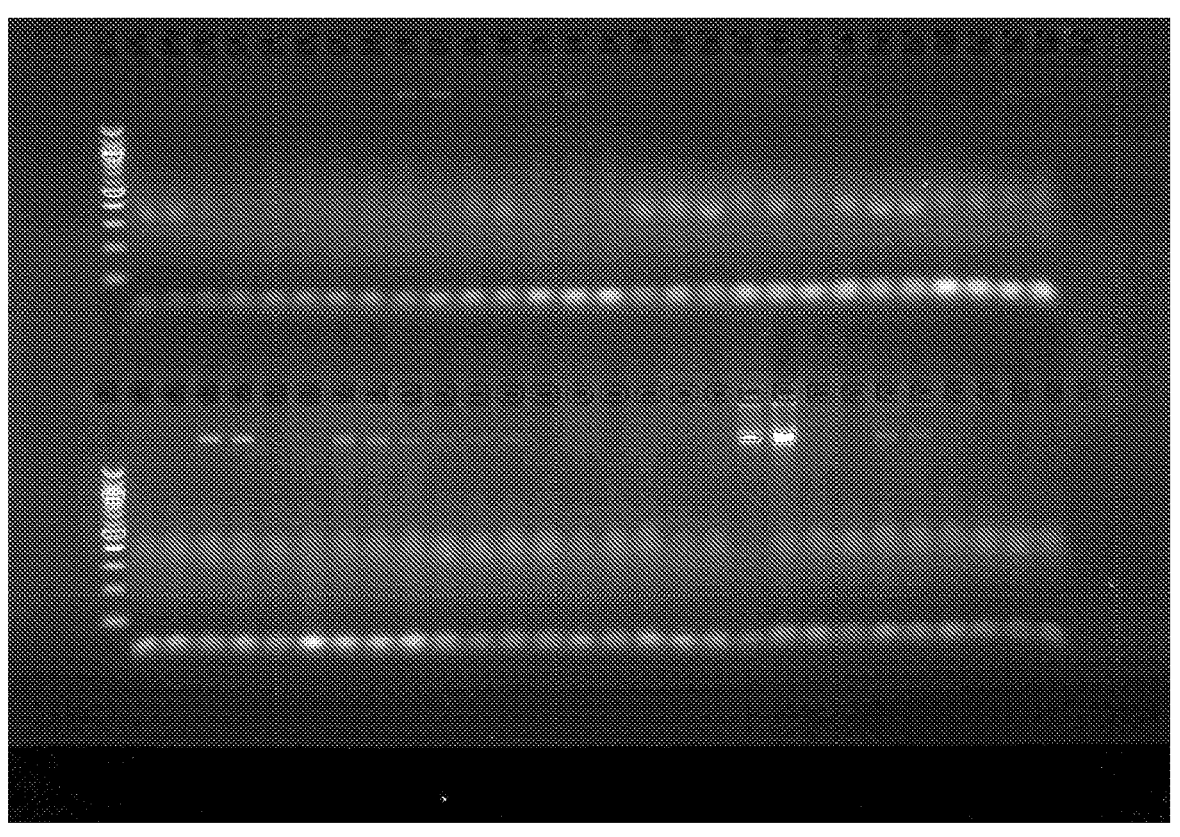
FIGS. 3 and 4 show the specificity of the method of the invention with standard matrices of a number of pathogens potentially present in the tested biological material as natural physiological flora, those which may result from co-infections or those which share similar genomic sequences, where
Figure 4:
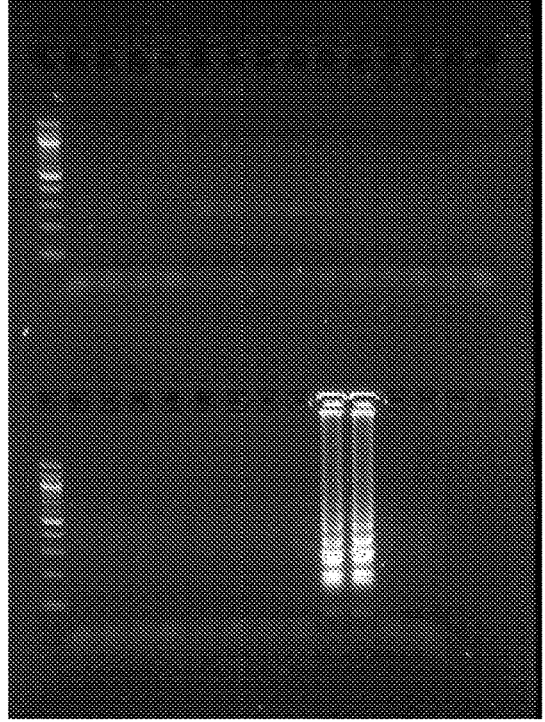

The sensitivity was determined by assaying serial dilutions of the *Neisseria gonorrhoeae* Quantitative DNA (ATCCR 700825DQ™) standard with a minimum amount of 10 copies of bacteria per reaction mixture, where the product amplification was measured in real time—FIG. 2 (Real-Time LAMP for serial dilutions).

The time required to detect the emitted fluorescence for individual samples is shown in Table 1.

The characterized primers allow for the detection of *Neisseria gonorrhoeae* bacteria by detecting the dcm gene fragment at a minimum number of 10 copies/reaction mixture.

TABLE 1

| Time required to detect fluorescence for each dilution of the *Neisseria gonorrhoeae* Quantitative DNA (ATCC ® 700825DQ ™) standard. | |
| --- | --- |
| Sample | Time to exceed the baseline fluorescence [min] |
| NG NTC | Undetermined |
| NG 10 copies | 18.94 |
| NG 20 copies | 17.49 |
| NG 50 copies | 15.61 |
| NG 100 copies | 14.25 |

The superiority of the amplification method and the oligonucleotides described in this specification over the tests based on the Real-Time LAMP technology is due to the much higher sensitivity, which is shown in FIG. 1 and the reduction of the analysis time shown in FIG. 2.

The invention claimed is:

1. A set of primers for amplifying the nucleotide sequence of the *Neisseria gonorrhoeae* dcm gene, characterized in that the set of primers contains a set of internal primers with the following nucleotide sequences a) and b), as well as a set of external primers containing the following sequences c) and d):

a) FIP primer comprising a 5' segment comprising 5' ATCTTTGGGGCTTGCGGGTG 3' (SEQ ID NO: 3) and a 3' segment comprising 5' TAAAGCGTGGGAT-GAACAGG 3' (SEQ ID NO: 4);

b) BIP primer comprising a 5' segment comprising 5' AAGCACGGGGCAAACGACTA 3' (SEQ ID NO: 5) and a 3' segment comprising 5' CAACTTCGCGTACCGTCAT 3' (SEQ ID NO: 6);

c) 5' TATGAGCCGGAACCGAGT 3' (SEQ ID NO: 1); and d) 5' TCGGGAAAGCCTTGGATTC 3' (SEQ ID NO: 2).

2. The set of primers of claim 1, characterized in that it further contains a set of loop primer sequences comprising 5' CCTGAAGCTTGGACGGTAAAAC 3' (SEQ ID NO:7) and 5' GCCGGCAAAGAAACACTATATCGG 3' (SEQ ID NO: 8).

3. A method of detecting *Neisseria gonorrhoeae* bacteria, characterized in that a selected region of the nucleic acid sequence of the bacterial genome is amplified using the set of primers as defined in claim 1, the amplification method being the LAMP method.

4. The method of detecting bacteria of claim 3, characterized in that the amplification is carried out with a temperature profile of:

69° C., 40 min.

5. The method of claim 4, characterized in that an end-point reaction is carried out with an additional temperature profile stage of 80° C., 5 min.

6. A kit for detecting infection with *Neisseria gonorrhoeae* bacterium, characterized in that it comprises a set of primers as defined in claim 1 in a tube.

7. The infection detection kit of claim 6, wherein the primers have the following concentrations:

primer c) at 0.12 µM, primer d) at 0.12 µM, primer b) at 0.96 µM, and primer a) at 0.96 µM.

8. The infection detection kit of claim 7, further comprising D-(+)-Trehalose dihydrate.

9. The infection detection kit of claim 7, further comprising a fluorescent marker capable of interacting with double-stranded DNA.

10. A method of detecting *Neisseria gonorrhoeae* bacteria, characterized in that a selected region of the nucleic acid sequence of the bacterial genome is amplified using the set of primers as defined in claim 2, the amplification method being the LAMP method.

11. The method of detecting bacteria of claim 10, characterized in that the amplification is carried out with a temperature profile of:

69° C., 40 min.

12. The method of claim 11, characterized in that an end-point reaction is carried out with a temperature profile of 80° C., for additional 5 min.

* * * * *